United States Patent [19]
White et al.

[11] Patent Number: 5,458,621
[45] Date of Patent: Oct. 17, 1995

[54] AUTOMATIC GAIN CONTROL AND METHOD FOR ENABLING DETECTION OF LOW AND HIGH AMPLITUDE DEPOLARIZATION ACTIVATION WAVES OF THE HEART AND ATRIAL DEFIBRILLATOR UTILIZING THE SAME

[75] Inventors: Harley White, Redmond; Joseph M. Bocek, Seattle, both of Wash.

[73] Assignee: InControl, Inc., Redmond, Wash.

[21] Appl. No.: 213,119

[22] Filed: Mar. 15, 1994

[51] Int. Cl.$^6$ .................................................. A61B 5/046
[52] U.S. Cl. .................................. 607/5; 607/4; 607/14; 128/705
[58] Field of Search .................................. 128/700, 702, 128/705, 708; 607/4, 5, 28

[56] References Cited

U.S. PATENT DOCUMENTS

5,010,887  4/1991  Thornander ............................ 128/708
5,269,300  12/1993  Kelly et al. ............................ 607/4
5,279,291  1/1994  Adams et al. ......................... 607/5
5,348,021  9/1994  Adams et al. ......................... 128/708

Primary Examiner—William E. Kamm
Assistant Examiner—Marianne Parker
Attorney, Agent, or Firm—Richard O. Gray, Jr.

[57] ABSTRACT

An apparatus reliably detects a depolarization activation wave of the heart. The apparatus includes a sensor in electrical contact with the heart for sensing electrical activity of the heart and including an amplifier for amplifying the sensed electrical activity according to a variable gain and providing a signal corresponding to the depolarization activation wave. The apparatus further includes an output circuit coupled to the sensor for producing an electrical output corresponding to the depolarization activation wave sensed by the sensor when the signal exceeds a threshold. The apparatus still further includes a control circuit coupled to the sensor and the output circuit for varying at least one of the gain and the threshold to maintain a predetermined sense margin between the sensed electrical activity and the gain and the threshold.

17 Claims, 2 Drawing Sheets

AUTOMATIC GAIN CONTROL AND METHOD FOR ENABLING DETECTION OF LOW AND HIGH AMPLITUDE DEPOLARIZATION ACTIVATION WAVES OF THE HEART AND ATRIAL DEFIBRILLATOR UTILIZING THE SAME

BACKGROUND OF THE INVENTION

The present invention generally relates to an apparatus and method for detecting a depolarization activation wave (R wave) of the heart. The present invention is more particularly directed to a fully automatic atrial defibrillator which employs automatic gain control to assure reliable detection of depolarization activation waves of the heart.

Atrial fibrillation is probably the most common cardiac arrhythmia. Although it is not usually a life-threatening arrhythmia, it is associated with strokes thought to be caused by blood clots forming in areas of stagnant blood flow as a result of prolonged atrial fibrillation. In addition, patients afflicted with atrial fibrillation generally experience palpitations of the heart and may even experience dizziness or even loss of consciousness.

Atrial fibrillation occurs suddenly and many times can only be corrected by a discharge of electrical energy to the heart through the skin of the patient by way of an external defibrillator of the type well known in the art. This treatment is commonly referred to as synchronized cardioversion and, as its name implies, implies applying cardioverting or defibrillating electrical energy to the heart in synchronism with the detected depolarization activation wave (R wave) of the heart. The treatment is very painful and, unfortunately, most often only results in temporary relief for patients, lasting but a few weeks.

Drugs are available for reducing the incidence of atrial fibrillation. However, these drugs have many side effects and many patients are resistant to them which greatly reduces their therapeutic effect.

Implantable atrial defibrillators have been proposed to provide relief to patients suffering from occurrences of atrial fibrillation. Unfortunately, to date, none of these atrial defibrillators have become a commercial reality, to the detriment of such patients.

Implantable atrial defibrillators proposed in the past have exhibited a number of disadvantages which probably have been the cause of these defibrillators failing to become a commercial reality. Two such proposed defibrillators, although represented as being implantable, were not fully automatic, requiring human interaction for cardioverting or defibrillating the heart. Both of these defibrillators require the patient to recognize the symptoms of atrial fibrillation with one defibrillator requiring a visit to a physician to activate the defibrillator and the other defibrillator requiring the patient to activate the defibrillator from external to the patient's skin with a magnet.

Synchronizing the delivery of the defibrillating or cardioverting electrical energy with a depolarization activation wave (R wave) of the heart is important to prevent ventricular fibrillation. Ventricular fibrillation is a fatal arrhythmia which can be caused by electrical energy being delivered to the heart at the wrong time in the cardiac cycle, such as during the T wave of the cycle. As a result, it is most desirable to sense depolarization activation waves of the heart to generate synchronization pulses (or signals) in a manner which avoids detecting noise as a depolarization activation wave. Also, it is desirable to sense depolarization activation waves in a manner which does not fail to detect extremely low amplitude depolarization activation waves but yet does not erroneously detect low amplitude noise such as T waves.

In addition to noise, a further problem in reliably detecting depolarization activation waves is the variability of the amplitudes of depolarization activation waves. Particularly during atrial fibrillation, depolarization activation waves are characterized by extreme variability. An extremely low amplitude depolarization activation wave may be followed immediately by an extremely high amplitude depolarization activation wave.

Depolarization activation waves are generally sensed as voltage threshold crossings. An atrial defibrillator includes an input sense amplifier in electrical contact with a patient's heart for sensing electrical activity of the heart. The sense amplifier amplifies the electrical activity according to a predetermined gain. A depolarization activation wave is detected when the amplified electrical activity exceeds a predetermined threshold.

Because of the variability in depolarization activation wave amplitude, some depolarization activation waves may be too small in amplitude to exceed the detection threshold of prior atrial defibrillators, meaning these depolarization activation waves may not be detected. Merely increasing the gain of the input sense amplifier which senses electrical activity of the heart does not provide a solution, since high amplitude depolarization activation waves may saturate the sense amplifier and provide sensing of undesirable signals such as the T wave. The apparatus and method of the present invention provides an approach to reliable detection of depolarization activation waves which accommodates extreme variability in depolarization activation wave amplitude.

SUMMARY OF THE INVENTION

The present invention therefore provides a method for reliably detecting a depolarization activation wave of the heart. The method includes the steps of providing a detection system having a variable sensitivity including a variable gain and a variable threshold. The method further includes the steps of sensing activity of the heart in at least one chamber of the heart and producing an input signal corresponding to the sensed activity, the input signal having an input amplitude. The method further includes the steps of amplifying the input signal according to the gain to produce an amplified input signal having an amplified input amplitude and producing an output when the amplified input signal exceeds the threshold, the output indicating the occurrence of the depolarization activation wave. The method still further includes the steps of varying at least one of the gain and the threshold to maintain a predetermined sense margin between the input amplitude and the gain and the threshold.

The present invention further provides an apparatus for reliably detecting a depolarization activation wave of the heart. The apparatus includes sensing means in electrical contact with the heart for sensing electrical activity of the heart and including amplifying means for amplifying the sensed electrical activity according to a variable gain and providing a signal corresponding to the depolarization activation wave. The apparatus further includes output means coupled to the sensing means for producing an electrical output corresponding to the depolarization activation wave sensed by the sensing means when the signal exceeds a threshold. The apparatus still further includes control means coupled to the sensing means and the output means for varying at least one of the gain and the threshold to maintain a predetermined sense margin between the sensed electrical activity and the gain and the threshold.

The present invention still further provides an implantable atrial defibrillator for reliably detecting a depolarization activation wave of the heart and applying cardioverting electrical energy to the atria of the heart in synchronism with the detected depolarization activation wave. The atrial defibrillator includes first detecting means adapted for sensing activity of the heart in at least one of the atria of the heart. The atrial defibrillator further includes atrial fibrillation detecting means responsive to the activity of the heart sensed by the first detecting means for determining when the atria of the heart are in need of cardioversion. The atrial defibrillator still further includes second detecting means for detecting ventricular activations of the heart, the second detecting means including sensing means for sensing electrical activity of the heart in at least one of the ventricles of the heart and including amplifying means for amplifying the sensed electrical activity according to a variable gain and providing a signal representative of the sensed electrical activity, and output means coupled to the sensing means for receiving the signal and producing an indication when the signal exceeds a threshold. The atrial defibrillator still further includes cardioverting means for applying cardioverting electrical energy to the atria of the heart when the atria of the heart are in need of cardioversion, the cardioverting means being responsive to the indication for applying the cardioverting electrical energy to the atria of the heart in predetermined time relation to a detected ventricular activation. The atrial defibrillator still further includes control means coupled to the sensing means and the output means for varying at least one of the gain and the threshold to maintain a predetermined sense margin between the sensed electrical activity and the gain and the threshold.

BRIEF DESCRIPTION OF THE DRAWINGS

The features of the present invention which are believed to be novel are set forth with particularity in the appended claims. The invention, together with further objects and advantages thereof, may best be understood by making reference to the following description taken in conjunction with the accompanying drawings, in the several figures of which like reference numerals identify identical elements, and wherein:

DETAILED DESCRIPTION OF THE PREFERRED EMBODIMENT

Figure 1:
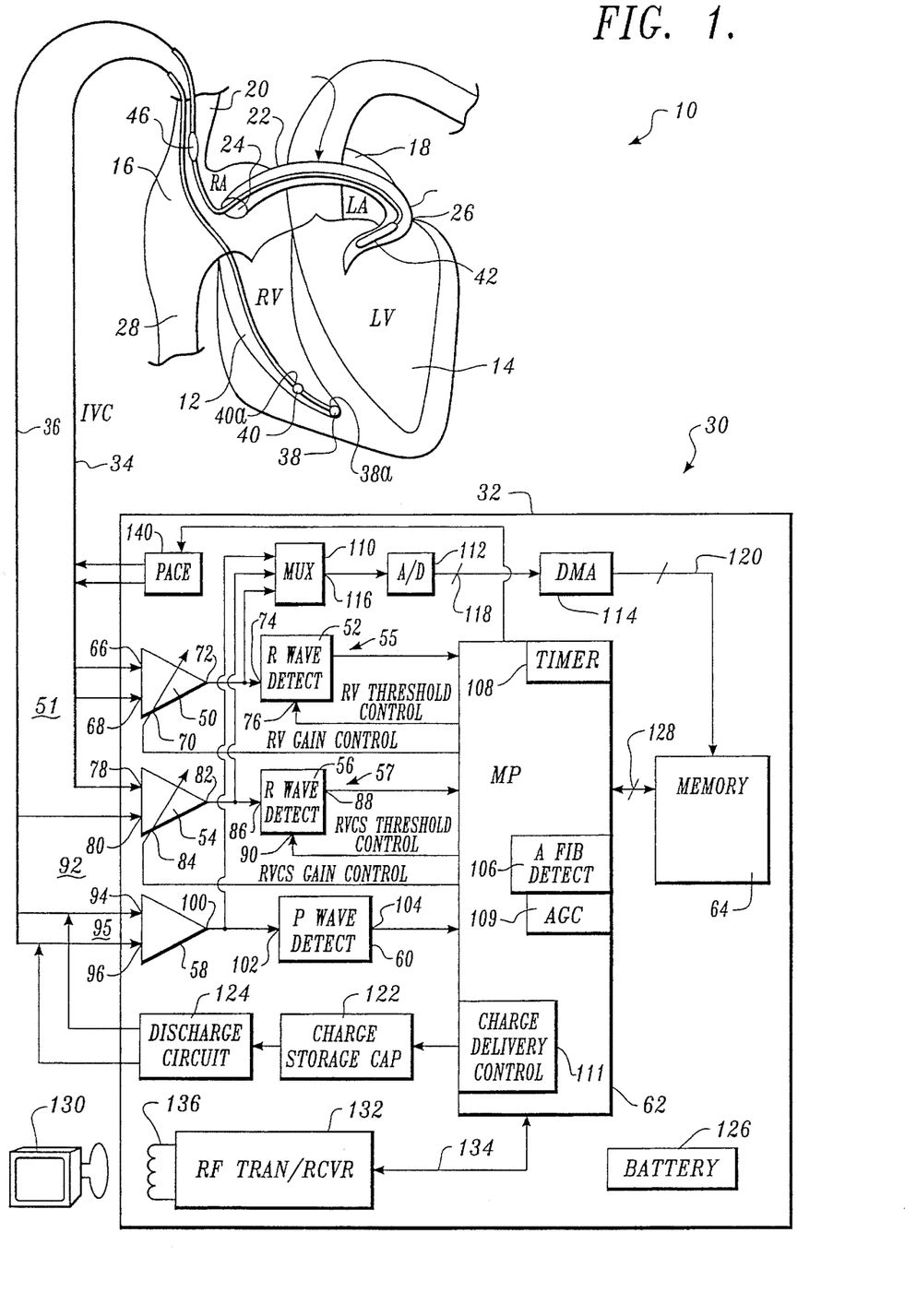
FIG. 1 is a schematic block diagram of a fully implantable atrial defibrillator embodying the present invention in accordance with a preferred embodiment thereof and shown in association with a human heart in need of atrial fibrillation monitoring and potential cardioversion of the atria.

Referring now to FIG. 1, it illustrates a fully implantable atrial defibrillator 30 embodying the present invention shown in association with a schematically illustrated human heart 10 in need of atrial fibrillation monitoring and potential cardioversion of the atria. The portions of the heart 10 illustrated in FIG. 1 are the right ventricle 12, the left ventricle 14, the right atrium 16, the left atrium 18, the superior vena cava 20, the coronary sinus 22, the coronary sinus ostium or opening 24, the left ventricular free wall 26, and the inferior vena cava 28. In addition, as used herein, the term "depolarization activation waves" denotes R waves of the heart cardiac cycle which induce depolarizations of the ventricles 12 and 14.

The atrial defibrillator 30 generally includes an enclosure 32 for hermetically sealing the internal circuit elements of the atrial defibrillator, an endocardial first lead 34 and an intravascular second lead 36. The second lead 36 may alternatively comprise two leads. A single lead is illustrated in FIG. 1 so as to not unduly complicate the figure. The enclosure 32 and the first and second leads 34 and 36 are arranged to be implanted beneath the skin of a patient so as to render the atrial defibrillator 30 fully implantable.

The endocardial first lead 34 preferably comprises an endocardial bipolar lead having electrodes 38 and 40 arranged for establishing electrical contact with the right ventricle 12 of the heart 10. The electrodes 38 and 40 permit bipolar sensing of depolarization activation waves in the right ventricle between a first pair of locations 38a and 40a within the right ventricle 12. As illustrated, the lead 34 is fed through the superior vena cava 20, into the right atrium 16, and then into the right ventricle 12. As will be appreciated by those skilled in the art, a second path for lead 34 could alternatively be through the inferior vena cava 28, into the right atrium 16, and then into the right ventricle 12.

The second lead 36 generally includes a first or distal electrode 42 and a second electrode 46. As illustrated, the second lead 36 is flexible and arranged to be passed down the superior vena cava 20, into the right atrium 16, into the coronary sinus ostium 24, and advanced into the coronary sinus 22 of the heart near the left side thereof so that the first or distal electrode 42 is within the coronary sinus or within a coronary vein, such as the great vein of the heart (not shown) adjacent to the left ventricle 14. The electrode 42 is preferably elongated such that the first electrode 42 is within the coronary sinus 22 or a coronary vein such as the great cardiac vein adjacent the left ventricle 14 as well as beneath the left atrium 18 near the left ventricle 14. The second electrode 46 is preferably located within either the right atrium 16 or the superior vena cava 20 and preferably within the right atrium 16.

As indicated above, the second lead 36 may comprise two leads. In this preferred embodiment, one of the two leads includes the first electrode 42 and the other of the two leads includes the second electrode 46. As noted above, the first electrode 42 and the second electrode 46 are illustrated in FIG. 1 as combined on a single lead, the second lead 36, so as not to unduly complicate the figure.

The first electrode 42 together with the second electrode 46 of the second lead 36 provide for the delivery of defibrillating or cardioverting electrical energy to the atria. Because the first electrode 42 is located beneath the left atrium 18 near the left ventricle 14 and the second electrode 46 is within either the right atrium 16 or the superior vena cava 20 and above the coronary sinus ostium 24, the electrical energy applied between these electrodes will be substantially confined to the atria 16 and 18 of the heart 10. As a result, the electrical energy applied to the right ventricle 12 and left ventricle 14 when the atria are cardioverted or defibrillated will be minimized.

Within the enclosure 32, the atrial defibrillator 30 includes a first sense amplifier 50, a first R wave detector 52, a second sense amplifier 54, a second R wave detector 56, a third sense amplifier 58 and a P wave detector 60. Within the enclosure 32, the atrial defibrillator 30 also includes a microprocessor 62 and a memory 64.

The first sense amplifier 50 includes a first input 66 which is coupled to electrode 38 of a first lead 34 and a second input 68 which is coupled to electrode 40 of the first lead 34. The first sense amplifier 50 also includes a gain input 70 coupled to the microprocessor 62. The first sense amplifier 50 amplifies the sensed electrical activity of the heart according to a variable gain received at the gain input 70 from the microprocessor, and provides at an output 72 an amplified input signal representative of the electrical activity of the heart such as depolarization activation waves sensed by the bipolar electrodes 38 and 40. The first sense amplifier 50 may include one or more gain stages, the gain of each gain stage being independently variable by the microprocessor 62. The first sense amplifier 50 may further include one or more filters for filtering sensed electrical activity of the heart.

The first R wave detector 52 includes an input 74 which is coupled to the output 72 of the first sense amplifier 50. The R wave detector 52 produces an electrical output corresponding to the depolarization activation wave sensed by the first sense amplifier 50 when the amplified input signal received at the input 74 of the first R wave detector 52 exceeds a threshold. The R wave detector 52 also includes a threshold input 76. The threshold input 76 is coupled to the microprocessor 62 for receiving a threshold value from the microprocessor 62.

As a result, the electrodes 38 and 40 and the first sense amplifier 50 form a sensing means 51 in electrical contact with the heart for sensing electrical activity of the heart including depolarization activation waves and including amplifying means for amplifying the sensed electrical activity according to a variable gain and providing a signal corresponding to the depolarization activation wave. The first R wave detector 52 forms an output means coupled to the sensing means for producing an electrical output corresponding to the depolarization activation wave sensed by the first sense amplifier 52 when the signal exceeds a threshold. The first sense amplifier 50 and the first R wave detector 52 form an RV channel 55.

The second sense amplifier 54 includes a first input 78 which is coupled to the electrode 42 of the second lead 36 and a second input 80 which is coupled to electrode 38 of the first lead 34. The second sense amplifier 54 also includes a gain input 84 coupled to the microprocessor 62 for receiving a gain value from the microprocessor 62. The second sense amplifier 54 amplifies the sensed electrical activity of the heart according to the gain value received from the microprocessor and provides at an output 82 an amplified signal representative of the electrical activity of the heart such as depolarization activation waves sensed by electrodes 38 and 40. The second sense amplifier 54 may include one or more gain stages, the gain of each gain stage being independently variable by the microprocessor 62. The second sense amplifier 54 may further include one or more filters for filtering sensed electrical activity of the heart.

The second R wave detector 56 includes an input 86 for receiving the amplified signal provided from the output 82 of the second sense amplifier 54. The second R wave detector 56 produces an electrical output at the output 88 when the amplified input signal provided at the input 86 exceeds a threshold. The second R wave detector 56 also includes a threshold input 90 coupled to the microprocessor 62 for receiving a threshold value from the microprocessor 62.

As a result, electrode 42, electrode 38, and sense amplifier 54 form a sensing means 92 in electrical contact with the heart 10 for sensing electrical activity of the heart 10 including depolarization activation waves and including amplifying means for amplifying the sensed electrical activity according to a variable gain and providing a signal corresponding to the depolarization activation waves. The second R wave detector 56 forms an output means coupled to the sensing means for producing an electrical output corresponding to the depolarization activation wave sensed by the sensing means when the signal exceeds a threshold. The second sense amplifier 54 and the second R wave detector 56 form an RVCS channel 57.

The third sense amplifier 58 senses electrical activity in the atria 16 and 18 of the heart 10. To that end, the third sense amplifier 58 includes a first input 94 which is coupled to electrode 46 and a second input 96 which is coupled to electrode 42. The third sense amplifier 58 includes an output 100 which is coupled to an input 102 of the P wave detector 60. The P wave detector 60 includes an output 104 for providing an indication of electrical activity of the heart sensed by the third sense amplifier 58. As a result, the electrodes 42 and 46 and the third sense amplifier 58 form a detecting means 95 adapted for sensing activity of the heart in at least one of the atria of the heart.

The microprocessor 62 includes an atrial fibrillation detector 106, a timer 108, an automatic gain control 109, and a charge delivery control 111. The atrial fibrillation detector 106 analyzes the electrical output of the first R wave detector 52, the second R wave detector 56 and the P wave detector 60 and the data stored in memory 64 corresponding to electrical activity of the heart sensed by first sense amplifier 50, second sense amplifier 54 and third sense amplifier 58; converted by analog-to-digital converter 112 and conveyed by direct memory access controller 114, and determines when the heart 10 is in need of cardioversion or defibrillation.

The atrial defibrillator 30 further includes an analog multiplexer 110, an analog-to-digital converter 112, and a direct memory access (DMA) controller 114. The output 72 of the first sense amplifier 50, the output 82 of the second sense amplifier 54, and the output 100 of the third sense amplifier 58 are coupled to the analog multiplexer 110. In response to control signals received from the microprocessor 62, the analog multiplexer 110 couples signals received from either the first sense amplifier 50, the second sense amplifier 54, or the third sense amplifier 58 to the output 116 of the analog multiplexer 110. The output 116 is coupled to the analog-to-digital converter 112, which converts analog signals received from the output 116 to digital data. The digital data are conveyed over a multiple bit data bus 118 to the direct memory access controller 114. The direct memory access controller 114 conveys the digital data, along with storage address information, over a multiple bit bus 120 to the memory 64. As a result, data received from either the first sense amplifier 50, the second sense amplifier 54 or the third sense amplifier 58 are stored by the DMA controller 114 in the memory 64, without further intervention by the microprocessor 62.

For determining if the heart 10 is in need of cardioversion or defibrillation, the atrial defibrillator 30 acquires an intracardiac electrogram (EGM) segment. To acquire an EGM segment, the microprocessor 62 conveys control signals to the analog multiplexer 110 to cause the analog multiplexer 110 to couple either the output 72 of the first sense amplifier 50 or the output 82 of the second sense amplifier 54 or the output 100 of the third sense amplifier 58 to the output 116 of the analog multiplexer. The analog-to-digital converter 112 converts analog signals from the output 116 to digital data. The DMA controller 114 receives the digital data from the output 118 of the analog-to-digital converter 112 and stores the data in the memory 64. The atrial defibrillator 30 stores data for a predetermined time duration, for example, eight seconds.

In this manner, the atrial defibrillator 30 may store data corresponding to electrical activity of the heart sensed by each of the first sense amplifier 50, the second sense amplifier 54 and the third sense amplifier 58. Following acquisition of an EGM segment by the atrial defibrillator 30, the atrial fibrillation detector 106 analyzes the data stored in the memory 64 to determine if the heart 10 is in need of cardioversion or defibrillation.

The atrial defibrillator 30 further includes a charger and storage capacitor circuit 122 of the type well known in the art which charges a storage capacitor to a predetermined voltage level and a discharge circuit 124 for discharging the storage capacitor within circuit 122 by a predetermined amount to provide a controlled discharge output of electrical energy when required to the atria of the heart 10. To that end, the discharge circuit 124 is coupled to the first electrode 44 and the second electrode 46 of the second lead 36 for applying the cardioverting or defibrillating electrical energy to the atria. The atrial defibrillator 30 further includes a depletable power source 126, such as a lithium battery, for providing power to the electrical components of the atrial defibrillator 30.

When the atrial fibrillation detector 106 determines that the atria 16 and 18 are in fibrillation and thus in need of cardioversion, the charge delivery control 111 causes the charger and storage capacitor circuit 122 to charge the storage capacitor within circuit 122. The charge delivery control 111 causes the discharge circuit 124 to discharge the capacitor of the circuit 122 for applying cardioverting electrical energy to the atria 16 and 18 in synchronism with an R wave detected by sense amplifier 50 and R wave detector 52 and second sense amplifier 54 and second R wave detector 56. The charge delivery control circuit 111 responds to the timer 108 to synchronize discharge of the capacitor to a detected R wave.

The microprocessor 62 is arranged to operate in conjunction with the memory 64, which may be coupled to the microprocessor 62 by a multiple bit address and data bus 128. This permits the microprocessor 62 to address desired memory locations within the memory for executing read or write operations. During a write operation, the microprocessor 62 stores data in the memory 64 at the addresses defined by multiple bit addresses conveyed over the multiple bit address and data bus 128 and conveys data to the memory 64. During a read operation, the microprocessor 62 obtains data from the memory 64 at the storage locations identified by the multiple bit addresses provided over the multiple bit address and data bus 128 and receives the data from the memory 64.

For entering operating parameters into the microprocessor 62, the microprocessor 62 receives programmable operating parameters from an external controller 130 which is external to the skin of the patient. The external controller 130 is arranged to communicate with a receiver/transmitter 132 within enclosure 32 which is coupled to the microprocessor 62 over a bi-directional bus 134. The receiver/transmitter 132 may be of the type well known in the art for conveying various information which it obtains from the microprocessor 62 to the external controller 130 or for receiving programing parameters from the external controller 130 which the receiver/transmitter 132 then conveys to the microprocessor 62 for storage in internal memory or in the memory 64 within enclosure 32.

The receiver/transmitter 132 includes a transmitting coil 136. Such communications circuits are well known in the art and may be utilized as noted above for receiving commands from external to the implantable enclosure 32 and for transmitting data to the external controller 130 from the implanted enclosure 32.

To complete the identification of the various structural elements within the enclosure 32, the atrial defibrillator 30 further includes a pace pulse delivery circuit 140. In response to signals received from the microprocessor 62, the pace pulse delivery circuit 140 generates a pacing pulse. The pace pulse delivery circuit 140 is coupled to the electrode 38 and the electrode 40 of lead 34 for the delivery of pacing pulses to the right ventricle.

For reliably detecting the occurrence of a depolarization activation wave in the RV channel, the atrial defibrillator 30 varies the gain of the first sense amplifier 50 or the threshold of the first R wave detector 52, or both. In accordance with the present invention, the atrial defibrillator 30 varies at least one of the gain of the first sense amplifier 50 and the threshold of the first R wave detector 52 to maintain a predetermined sense margin between the amplitude of the signal sensed at the inputs 66, 68 of the first sense amplifier 50 and the gain of the first sense amplifier 50 and the threshold of the first R wave detector 52.

Similarly, for reliably detecting the occurrence of a depolarization activation wave in the RVCS channel, the atrial defibrillator 30 varies the gain of the second sense amplifier 54 or the threshold of the second R wave detector 56, or both. In accordance with the present invention, the atrial defibrillator 30 varies at least one of the gain of the second sense amplifier 54 and the threshold of the second R wave detector 56 to maintain a predetermined sense margin between the amplitude of the signal sensed at the inputs 78, 80 of the second sense amplifier 54 and the gain of the second sense amplifier 54 and the threshold of the second R wave detector 56.

The sensitivity of a detection circuit is the minimum amplitude (in mV) of an input signal applied to the detection circuit that will cause a threshold event in the detection circuit with a fixed gain and a fixed detection threshold. The sense margin of the detection circuit is the ratio of the amplitude of the input signal to the sensitivity of the detection circuit. For example, in a detection circuit with a sense margin of 2:1, an input which produces a detected output has twice the amplitude necessary to cause a detection. Where the detection circuit includes both gain stages and threshold detection stages, the sense margin of the detection circuit depends on both the gain of the gain stage and the threshold of the threshold detection stage. Thus, the sense margin of the RV channel 55 depends on both the gain of the first sense amplifier 50 and the threshold of the first R wave detector 52. The sense margin of the RVCS channel 57 depends on both the gain of the second sense amplifier 54 and the threshold of the second R wave detector 56.

Figure 2:
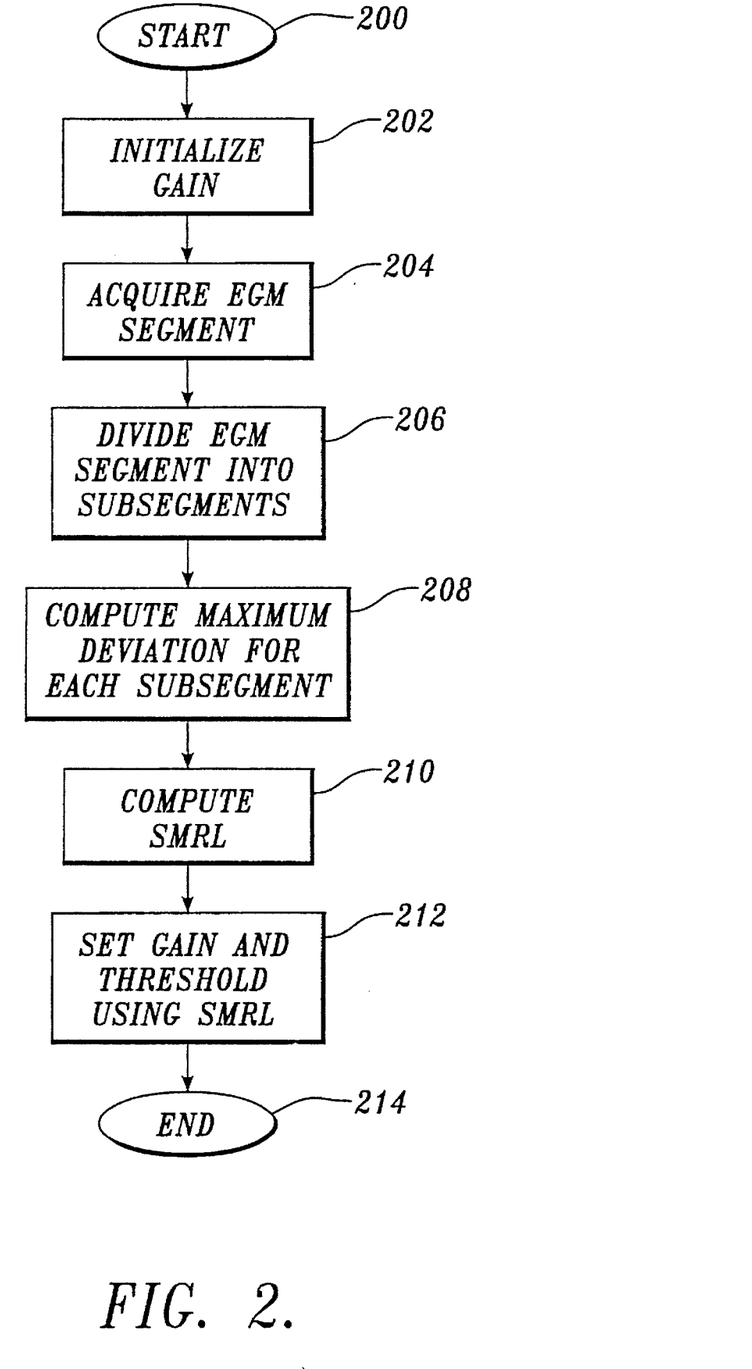
FIG. 2 is a flow diagram illustrating the manner in which the atrial defibrillator of FIG. 1 may be implemented in accordance with the present invention for reliably detecting depolarization activation waves of the heart.

Referring now to FIG. 2, it is a flow diagram illustrating the manner in which the atrial defibrillator 30 of FIG. 1 may be implemented in accordance with the present invention for reliably detecting a depolarization activation wave of the heart 10. The method begins at step 200. At step 202, the microprocessor 62 sets the programmable gain in the first sense amplifier 50 to an initial gain value, for example, a minimum gain value.

At step 204, automatic gain control 109 of the microprocessor 62 begins the acquisition of a digitally quantized RV electrocardiogram (EGM) segment via the DMA process. The microprocessor 62 configures the analog multiplexer 110 to couple the output 72 of the first sense amplifier 50 to the analog-to-digital converter 112. The analog-to-digital converter 112 converts to digital data the analog signals produced by the first sense amplifier 50. The DMA controller 114 stores the digital data in the memory 64. Preferably, data are stored which correspond to electrical activity of the heart during a first predetermined time duration, for example, eight seconds.

At step 206, automatic gain control 109 of the microprocessor 62 begins analyzing the EGM segment data stored in the memory 64. Preferably, the automatic gain control 109 divides the data stored during the predetermined time duration into data corresponding to a plurality of time segments. For example, the automatic gain control 109 may divide the eight-second time duration into four equal two-second time segments, $W_1$, $W_2$, $W_3$ and $W_4$.

At step 208, the automatic gain control 109 rectifies or determines the absolute value of the data for each of the plurality of time segments. The automatic gain control 109 also determines the value of the peak deviation from a predetermined base line of the rectified data during each time segment of the plurality of time segments. The predetermined base line may be, for example, 0 volts. The peak deviations correspond to R waves detected by the RV channel 55. For example, the automatic gain control 109 may compute four peak deviation values $M_1$, $M_2$, $M_3$ and $M_4$ for the four time segments.

At step 210, the automatic gain control 109 determines a sense margin reference level by averaging a predetermined number of the peak deviations determined in step 208. Any number or combination of peak deviations of the stored data could be averaged to determine a sense margin reference level. However, in order to minimize the effects of extreme values of stored data, the automatic gain control 109 preferably determines the sense margin reference level by averaging the least of a first peak deviation determined during a first time segment and a second peak deviation determined during a second time segment, and the least of a third peak deviation determined during a third time segment and a fourth peak deviation determined during a fourth time segment. For example, sense margin reference level (SMRL) may be determined according to the following equation:

$$SMRL = \frac{\min(M_1, M_2) + \min(M_3, M_4)}{2}$$

At step 212, the automatic gain control 109 adjusts the gain of the first sense amplifier 50 and the threshold of the first R wave detector 52 so that the sense margin is maintained at a predetermined value, for example, 2:1. The sense margin is the ratio between the sense margin reference level, determined at step 210, and the threshold of the first R wave detector 52. Thus, the sense margin (SM) is determined according to the following equation:

$$SM = \frac{SMRL}{\text{Detection Threshold}} = 2:1$$

Since the sense margin reference level was determined using data corresponding to electrical activity of the heart amplified by the first sense amplifier 50, the sense margin reference level is a function of the gain of the first sense amplifier 50. The gain and the threshold are preferably selected using table lookup such that the sense margin is as close to 2:1 as possible without being less than 2:1. The method concludes at step 214.

After completing the method in accordance with the present invention, the microprocessor 62 controls the atrial defibrillator 30 to acquire a new EGM segment and store data in the memory 64 corresponding to sensed electrical activity of the heart during a second predetermined time duration, for example, eight seconds. This data is acquired using a gain value for the first sense amplifier 50 and a threshold value for the first R wave detector 52 which have been adjusted in accordance with the method of the present invention to maintain a predetermined sense margin. This data may be used, for example, by the atrial fibrillation detector 106 to determine if the heart 10 is in atrial fibrillation and in need of cardioversion or defibrillation.

After completing the method to set a first valid sense margin and acquiring an EGM segment with this valid sense margin, step 202 need not be repeated. But rather, step 204 may be executed using the gain and threshold most recently set at step 212. If the execution of steps 206–212 does not indicate a change in gain nor a change in threshold from the previous gain and previous threshold, then the EGM segment acquired by step 204 was acquired with the appropriate sense margin. This data may then be used by other analysis algorithms associated with the atria defibrillator 30, eliminating the requirement for these algorithms to acquire an additional EGM segment in such cases.

The method illustrated in FIG. 2 may also be repeated for the RVCS channel 57. The automatic gain control 109 may adjust the gain of the second sense amplifier 54 and the threshold of the second R wave detector 56 in accordance with the method illustrated in FIG. 2.

The method of the present invention may be repeated at predetermined times during operation of the atrial defibrillator 30. For example, the atrial defibrillator 30 may generally remain in a resting state, wherein the electrical components of the atrial defibrillator 30 are deenergized in order to conserve energy stored in the battery 116. At predetermined time intervals, the atrial defibrillator 30 may change from the resting state to an awake state, during which electrical activity of the heart 10 is sensed in order to determine if the heart 10 is in need of defibrillation or cardioversion. If it is not determined that the heart 10 is in need of defibrillation or cardioversion, the atrial defibrillator 30 may return to the resting state. If it is determined that the heart 10 is in need of defibrillation or cardioversion, the charge delivery control 111 initiates charging of the storage capacitor in the circuit 122. When the storage capacitor is charged to a predetermined level, the discharge circuit 124 may discharge the storage capacitor to provide cardioverting or defibrillating electrical energy to the atria of the heart 10.

The method of the present invention may be repeated each time the atrial defibrillator 30 changes from the resting state to the awake state in order to recalibrate the first and second sense amplifiers 50, 54 and the first and second R wave detectors 52, 56. The method in accordance with the present invention may also be repeated after the storage capacitor is charged but just prior to delivering the cardioverting or defibrillating electrical energy to the heart, as a safety check to confirm the detected atrial fibrillation or other arrhythmia condition.

Either the sensitivity or the sense margin of the RV channel 55 or the RVCS channel 57 may be varied using the external controller 130. A selected sensitivity or sense margin value may be communicated to the receiver/transmitter 132 within the enclosure 32. The selected sense margin value is then communicated by the receiver/transmitter 132 to the microprocessor 62 over the bi-directional bus 134.

As can be seen from the foregoing, the present invention provides a method and apparatus for reliably detecting a depolarization activation wave of the heart by automatically adjusting either the gain of a sense amplifier or the threshold of a threshold detector to maintain a predetermined sense margin. The present invention allows detection of depolarization activation waves of the heart despite wide variations in the amplitudes of the depolarization activation waves.

While a particular embodiment of the present invention has been shown and described, modifications may be made. For example, the method and apparatus of the present invention may be utilized to advantage in implantable cardiac devices other than atrial defibrillators. Hence, it is therefore intended in the appended claims to cover all such changes and modifications which fall within the true spirit and scope of the invention.

I claim:

1. A method for reliably detecting a depolarization activation wave of a heart, the method including the steps of:

providing a detection system having a gain and a threshold;

sensing activity of the heart in at least one chamber of the heart and producing an input signal corresponding to said sensed activity, said input signal having an input amplitude;

amplifying said input signal according to said gain to produce an amplified input signal having an amplified input amplitude;

producing an output when said amplified input signal exceeds said threshold, said output indicating an occurrence of said depolarization activation wave; and varying at least one of said gain and said threshold to maintain a predetermined sense margin between said input amplitude and said gain and said threshold.

2. A method as defined in claim 1 further including the steps of:

sensing said activity of the heart during a predetermined time duration;

determining a plurality of peak deviations of said amplified input amplitude from a predetermined baseline during said predetermined time duration;

determining a reference sense margin from said plurality of peak deviations; and determining said sense margin from a ratio of said reference sense margin to said threshold.

3. A method as defined in claim 2 further including the steps of dividing said predetermined time duration into a plurality of time segments and determining a peak deviation of said amplified input amplitude from said predetermined baseline during each time segment of said plurality of time segments to form said plurality of peak deviations.

4. A method as defined in claim 3 further including the step of averaging a predetermined number of peak deviations of said plurality of peak deviations to determine said reference sense margin.

5. A method as defined in claim 4 further including the step of averaging a least one of a first peak deviation determined during a first time segment and a second peak deviation determined during a second time segment and a least one of a third peak deviation determined during a third time segment and a fourth peak deviation determined during a fourth time segment to determine said reference sense margin.

6. An apparatus for reliably detecting a depolarization activation wave of a heart, the apparatus comprising:

sensing means in electrical contact with the heart for sensing electrical activity of the heart and including amplifying means for amplifying said sensed electrical activity by a gain and providing a signal;

threshold means coupled to said amplifying means for producing an electrical output when said signal exceeds a threshold; and control means coupled to said sensing means and said threshold means for varying at least one of said gain and said threshold to maintain a predetermined sense margin between said sensed electrical activity and said gain and said threshold.

7. An apparatus as defined in claim 6 further comprising conversion means coupled to said sensing means for converting said signal to digital data and memory means for storing said digital data during a predetermined time duration.

8. An apparatus as defined in claim 7 wherein said control means is coupled to said storage means for receiving said stored digital data and wherein said control means varies said gain and said threshold in response to said digital data.

9. An apparatus as defined in claim 8 wherein said control means includes processing means for determining a plurality of peak values of said digital data during said predetermined time duration and averages a predetermined number of said plurality of peak values to determine a sense margin reference level, said control means varying at least one of said gain and said threshold in response to said sense margin reference level.

10. An apparatus as defined in claim 9 wherein said processing means determines said sense margin from a ratio of said sense margin reference level and said threshold.

11. An implantable atrial defibrillator for applying cardioverting electrical energy to the atria of a heart in synchronism with a detected depolarization activation wave, the atrial defibrillator comprising:

detecting means for sensing activity of the heart in at least one of the atria of the heart;

atrial fibrillation detecting means responsive to activity of the heart sensed by said detecting means for determining when the atria of the heart are in need of cardioversion;

an apparatus for detecting a depolarization activation wave of the heart, said apparatus including sensing means in electrical contact with the heart for sensing electrical activity of the heart and including amplifying means for amplifying said sensed electrical activity by a gain and providing a signal, threshold means coupled to said amplifying means for producing an electrical output when said signal exceeds a threshold, and control means coupled to said sensing means and said threshold means for varying at least one of said gain and said threshold to maintain a predetermined sense margin between said sensed electrical activity and said gain and said threshold; and cardioverting means for applying cardioverting electrical energy to the atria of the heart when the atria of the heart are in need of cardioversion and responsive to said electrical output.

12. An atrial defibrillator as defined in claim further comprising conversion means coupled to said sensing means for converting said signal to digital data and memory means for storing said data.

13. An atrial defibrillator as defined in claim 12 wherein said control means includes processing means coupled to said storage means for receiving said data and determining a peak value of said data for each time segment of a predetermined number of time segments to form a plurality of peak values, said control means varying at least one of said gain and said threshold in response to said plurality of peak values.

14. An atrial defibrillator as defined in claim 13 wherein said processing means averages a predetermined number of peak values of said plurality of peak values to determine a sense margin reference level, and wherein said processing means determines said sense margin from a ratio of said sense margin reference level and said threshold.

15. An atrial defibrillator as defined in claim 14 wherein said processing means determines a first peak value during a first time segment, a second peak value during a second time segment, a third peak value during a third time segment and a fourth peak value during a fourth time segment and wherein said processing means averages a least one of said first peak value and said second peak value and a least one of said third peak value and said fourth peak value to determine said sense margin reference level.

16. An atrial defibrillator as defined in claim 15 wherein said control means varies at least one of said gain and said threshold to maintain said ratio substantially equal to a predetermined number.

17. An atrial defibrillator as defined in claim 16 wherein said control means maintains said ratio substantially equal to 2.

* * * * *

UNITED STATES PATENT AND TRADEMARK OFFICE
CERTIFICATE OF CORRECTION

PATENT NO. : 5,458,621

DATED : October 17, 1995

INVENTOR(S) : Harley White and Joseph M. Bocek

It is certified that error appears in the above-indentified patent and that said Letters Patent is hereby corrected as shown below:

| Column | Line | |
|--------|------|--|
| 13 | 4 | insert --11-- after "claim" |

Signed and Sealed this

Twentieth Day of February, 1996

BRUCE LEHMAN

Attest:

Attesting Officer

Commissioner of Patents and Trademarks